United States Patent [19]

Mahruki

[11] Patent Number: 4,592,347

[45] Date of Patent: Jun. 3, 1986

[54] RETRACTION DEVICE

[76] Inventor: Nimetullah M. T. Mahruki, Ortaköy, Palanga Cad. No: 15 Süreyya Ap., Istanbul, Turkey

[21] Appl. No.: 678,063

[22] Filed: Dec. 4, 1984

[30] Foreign Application Priority Data

Dec. 13, 1983 [TR] Turkey ................................. 146082

[51] Int. Cl.⁴ ............................................... A61F 5/46
[52] U.S. Cl. ..................................... 128/127; 128/321
[58] Field of Search ............... 128/130, 131, 129, 128, 128/127, 321, 353, 346; 604/14; 81/415, 345, 417, 355, 321

[56] References Cited

U.S. PATENT DOCUMENTS

| | | | |
|---|---|---|---|
| 463,785 | 11/1891 | Connable et al. | 128/321 |
| 1,070,559 | 8/1913 | Toth | 81/417 |
| 2,060,366 | 11/1936 | Dunlap | 128/321 |
| 2,518,994 | 8/1950 | Miller | 128/321 |
| 2,539,852 | 1/1951 | McCoy | 81/354 |
| 2,553,479 | 5/1951 | Schmarje et al. | 81/345 |
| 2,637,320 | 5/1953 | Greenberg | 128/323 |
| 3,022,787 | 2/1962 | Daniel | 128/321 |
| 3,254,649 | 6/1966 | Wood | 128/321 |
| 3,613,683 | 10/1971 | Kees, Jr. et al. | 128/321 |
| 3,635,215 | 1/1972 | Shea et al. | 128/130 |
| 3,877,434 | 4/1975 | Ferguson et al. | 128/346 |
| 4,106,508 | 8/1978 | Berlin | 128/346 |

FOREIGN PATENT DOCUMENTS 65054 11/1982 European Pat. Off. ............ 128/321

*Primary Examiner*—Robert Peshock
*Assistant Examiner*—Cary E. Stone
*Attorney, Agent, or Firm*—Evelyn M. Sommer

[57] ABSTRACT

A reusable retraction device is provided which is adapted to remove an object such as, for example, a vaginal sponge from a woman's vagina. The retraction device comprises an outer barrel open at both its upper and lower ends and having a center aperture passing through the center thereof. Retraction element is provided within the barrel and extend from its upper end. The retraction element is adapted to open and close to permit gripping and release of the sponge after insertion of the barrel into the vagina. The opening and closing of the retraction element is achieved using control, i.e. gripping elements which extend outwardly from the lower end of the barrel and are in substantially the same plane as the barrel.

16 Claims, 16 Drawing Figures

RETRACTION DEVICE

BACKGROUND OF THE INVENTION

The present invention relates generally to a retraction device and, more particularly, to such a retraction device adapted to remove or retract vaginal sponges, particularly chemically impregnated vaginal sponges, from the vagina of a woman. The retraction device of the present invention is adapted be used by an untrained person without professional assistance.

Devices heretofore used for the removal of vaginal sponges from the human vagina were, oftentimes, incapable of being used without professional assistance due to the complexity of their structure and the possibility of damage or irritation to the vaginal mucosa if improperly used. As such, these devices could only be used by a trained professional. Other, less complex devices which did not present such difficulties, were incapable of being sterilized prior to use and, as such, were potential sources of infection.

Against the foregoing background, it is a primary object of the present invention to provide a retraction device for removing vaginal sponges from the human vagina.

It is another object of the present invention to provide such a retraction device which is relatively simple in structure and which can be used without the assistance of a trained professional.

It is still another object of the present invention to provide such a retraction device which will not injure the vaginal mucosa during use.

It is yet another object of the present invention to provide such a retraction device which is able to be sterilized prior to each use.

SUMMARY OF THE INVENTION

To the accomplishments of the foregoing objects and advantages, the present invention, in brief summary, comprises a reusable retraction device which is adapted to remove a vaginal sponge from a woman's vagina. The retraction device comprises an outer barrel which is adapted to be inserted into the vagina of a woman for effecting removal of the sponge. The barrel is open at both its upper and lower ends and has a center aperture passing through the center thereof. Moveable retraction means are provided within the barrel extending between the upper and lower ends thereof. The retraction means include a retraction element which extends outwardly from the upper end of the barrel and which is adapted to open and close to permit gripping and release of the sponge. The retraction means further include control means which extend outwardly from the lower end of the barrel and which control the opening and closing of the retraction element.

Three embodiments of the retraction device of the present invention are provided. In the first embodiment, the retraction device comprises an outer barrel open at its upper and lower ends with a longitudinally extending center aperture extending between the ends. A transverse pin retaining aperture is further provided which is adapted to receive a retaining pin. A tubular piston is positioned within the outer barrel and is adapted to travel toward and away from the upper end of the barrel. The tubular piston is open at its upper end and includes gripping means at its opposed lower end. It further includes a pair of opposed, longitudinally extending, keyway slots each proximately spaced from the upper end of the piston and adapted to permit the retaining pin to pass therethrough in order to capture the piston within the barrel. A spring-loaded retraction element is further provided within the open upper end of the piston. The retraction element has a pair of gripping edges and means for securing the retraction element to the retaining pin. The gripping edges are adapted to close when the piston is moved toward the upper end of the barrel and open when the piston is withdrawn from said upper end.

An alternative embodiment of the retraction device of the present invention comprises an outer barrel open at its upper and lower ends with a longitudinally extending center aperture extending between the open ends. A retraction element contained within the barrel is further provided. The retraction element, which extends out of both the upper and lower ends, includes a pair of spring loaded, arm portions having normally closed gripping edges at their upper ends and normally separated gripping handles at their lower ends. The gripping edges are adapted to be opened for gripping a sponge when the gripping handles are forced together. Due to the spring loading, when the force bringing the handles together is released, the handles are permitted to return to their normally separated position resulting in the gripping edges returning to their normally closed position.

In a still further embodiment, the retraction device comprises an outer barrel open at both its upper and lower ends and having a longitudinally extending center aperture extending between said ends which is adapted to receive a movable piston. A longitudinally extending keyway is provided in the barrel which opens into the center aperture thereof. The barrel has a hook tip at its upper end. A movable piston is contained within the outer barrel and is adapted to travel toward and away from the upper end of the barrel. The piston includes an outwardly projecting tongue adapted to travel along the keeway as the piston is moved toward and away from the upper end. It is further adapted to engage the hook tip for gripping the sponge when the piston is fully inserted into the barrel and be drawn away from the hook tip and release the sponge when the piston is retracted from the barrel.

BRIEF DESCRIPTION OF THE DRAWINGS

The foregoing and still other objects and advantages of the present invention will be more apparent from the following detailed explanation of the preferred embodiments of the invention in connection with the accompanying drawings, wherein.

DETAILED DESCRIPTION OF THE PREFERRED EMBODIMENTS

Figure 1:
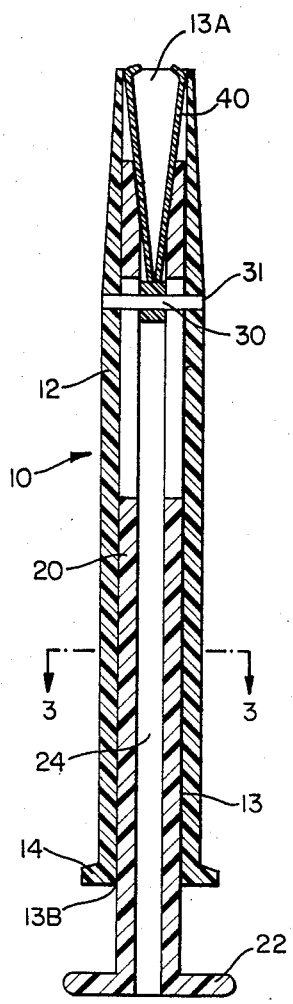
FIG. 1 is a side elevational view in section of one embodiment of the retraction device of the present invention with the retraction elements in an open position.

FIGS. 1-9 illustrate one embodiment of the retraction device of the present invention. As shown, in particular, in FIGS. 1-4, the retraction device of the first embodiment of the present invention, referred to generally by reference numeral 10, includes an elongated tubular outer tube or barrel 12 which contains a movable piston 20 provided therein. Elongated tubular barrel 12 includes a longitudinally extending center aperture 13 passing through the center thereof which opens at opposed upper and lower ends 13A and 13B of the barrel, respectively. Open upper end 13A is conically shaped to facilitate insertion of the barrel 12 into the vagina by tapering the thickness of the barrel 12 at the upper end 13A thereof. A gripping flange 14 is provided about the lower end 13 of the barrel 12 to facilitate gripping by the user during use.

A pin 30 is provided within the barrel 12 extending transversely from one wall of the barrel 12 to the other and through the center aperture 13 contained therein. Pin 30 serves to secure one or more retraction elements 40 to the barrel 12 and to the movable piston 20.

Figure 2:
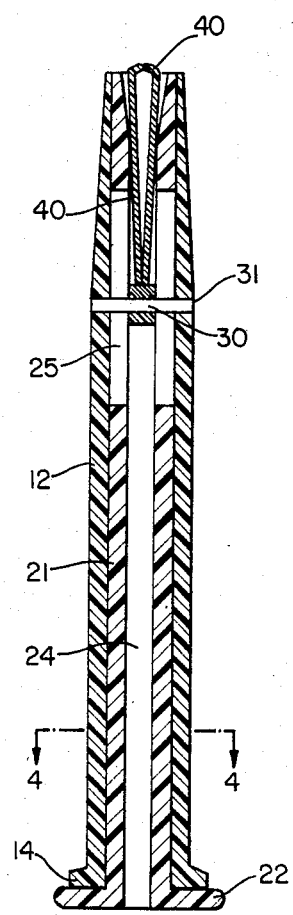
FIG. 2 is a side elevational view in section of the retraction device of FIG. 1 with the retraction elements in a closed or gripping position.
Figure 5:
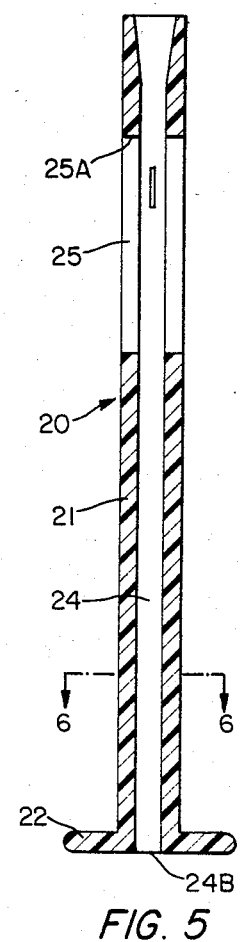
FIG. 5 is a side elevational view in section of the piston of the retraction device of the FIG. 1.
Figure 6:
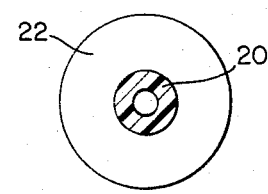
FIG. 6 is a sectional view taken along line 5—5 of FIG. 5.

Movable piston 20, which is shown outside of its normal position within the barrel 12 in FIGS. 5-6, includes an elongated shaft 21 having a T-shaped gripping handle 22 provided its lower end. A longitudinally extending center aperture 24 is further provided which passes through the center of the elongated shaft 21. The center aperture 24 is open at both its upper end 24A and at its lower end 24B. Upper end 24A of the center aperture 24 has a gradual outward flare. The diameter of the elongated piston shaft 21 is slightly less than the diameter of the center aperture 13 of the barrel 12 to permit the piston 20 to move back and forth within the center aperture 13. A pair of elongated, opposed "sliding motion" keyway slots 25 extending outwardly from the center aperture 24 are provided in opposite walls of the piston shaft 21 to accommodate transverse insertion of the pin 30 as shown in FIGS. 1 and 2. By making the keyway slots 25 elongated, the piston 20 is able to move within the barrel 12 without necessitating moving the pin 30.

The piston 20 is adapted to be fully inserted into the barrel 12 when the gripping handle 22 of the piston 20 contacts the gripping flange 14 at the bottom of the barrel 12. Similarly, retraction of the piston 20 out of the barrel 12 is limited by contact between the pin 30 and the upper limit 25A of the keyway slots 25.

Figure 7:
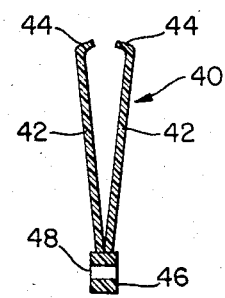
FIGS. 7-9 are side elevational views in section of the retraction elements which may be used in conjunction with the retraction device of FIG. 1 shown in different positions outside of the retraction device.
Figure 8:
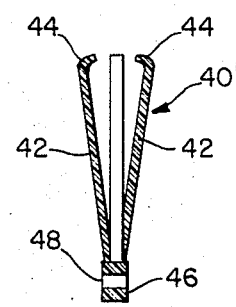
Figure 9:
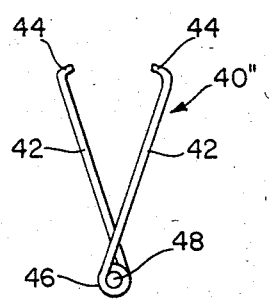

Three different types of retraction elements 40, 40' and 40" which may be used in conjunction with the retractor 10 of FIGS. 1-9 are illustrated in FIGS. 7-9. Each of the retraction elements includes a pair of opposed arm portions 42 having gripping edges 44 at their upper ends. Retainers 46 are provided at the intersection of the arm portions 42 of each type of retraction elements 40, 40' and 40" with a transverse pin aperture 48 passing through the center of each retainer 46 adapted to receive the pin 30 therethrough for retaining the respective retraction element 40, 40' and 40" within the retraction device 10.

The retraction elements 40 are springs, preferably stainless steel springs. The springs may, if desired, be coated with a plastic coating to reduce the possibility of infection and mucosa damage during use. In their normal "open" position, the gripping edges 44 of the retraction elements 40 are spread apart. The gripping edges 44 may, however, be closed as shown in FIGS. 1 and 2 by further inserting the piston 20 into the barrel 12 which causes the upper walls of the piston 20 to pass between the interior walls of the barrel 12 and the retraction elements 40 thereby reducing the diameter thereof and, consequently, forcing the gripping edges 44 together.

For purposes of assembly, the piston 20 is inserted into the open lower end 13B of the barrel 12. One of the retraction elements 40 is then introduced into the retraction device 10 through the open upper end 13A of the barrel 12 and secured therein by inserting pin 30 through the pair of transverse apertures 31 contained in opposed walls of the barrel 12, through the opposed keyway slots 25 of the piston 20 and through the pin aperture 48 in the retainer 46 of the retraction element 40. In this manner, while the retraction element 40 is secured within the retraction device 10, the piston 20 can be moved to the predetermined limits previously described.

Figure 3:
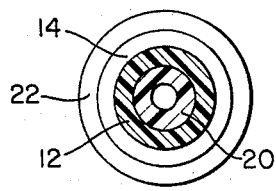
FIG. 3 is a sectional view taken along lines 1—1 of FIG. 1.
Figure 4:
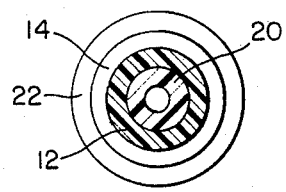
FIG. 4 is a sectional view taken along line 2—2 of FIG. 2.

It will be appreciated that the retraction device 10 of the present invention is adapted to function in the following manner. After insertion of the piston 20 into the barrel 12 and securing of the retraction element 40 thereto by the use of the pin 30, the retraction device 10 is ready for use. The piston 20 is withdrawn using the gripping handle 22 thereof to a position as shown in FIGS. 1 and 3. By partially withdrawing the piston 20 from the barrel 12, the upper walls of the piston 20 move away from the open upper end 13A of the barrel 12 thus permitting the arm portions 42 of the retraction element 40 to spread against the center aperture of the barrel 12 and "open" the gripping edges 44. The retraction device 10 may then be inserted into the vagina of a woman until it comes into contact with the sponge to be gripped. Upon contact between the retraction device 10 and the sponge (not shown), the piston 20 is re-inserted into the barrel 12 by compressing the gripping handles 22 of the piston 20 against the flange 14 of the barrel 12. This forces the upper walls of the piston 20 up and around the arms 42 of the retaining element 40 which causes the gripping edges 44 to "close" and grip the sponge. The retraction device 10 may then be withdrawn from the vagina with a portion of the sponge captured between gripping edges 44.

The mounting of the retraction element 40 on pin 30 which passes transversely through the keyway slots 25 in piston 20 permits the piston 20 to act in the desired manner and further permits smooth removal of the sponge from the vagina.

The retraction device 10 of the embodiment of FIGS. 1-9 can be re-used by sterilizing the retraction device between uses.

Figure 10:
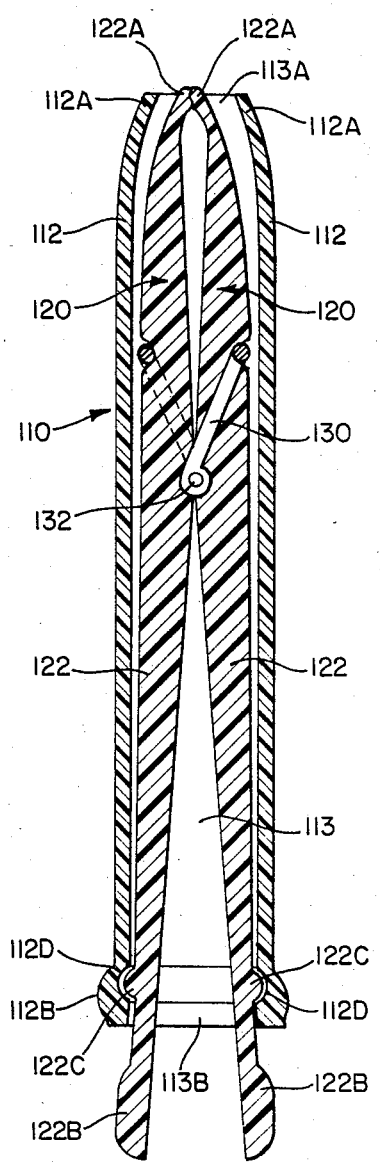
FIG. 10 is a side elevational view in section of an alternative embodiment of the retraction device of the present invention with the retraction elements shown in a closed position.
Figure 11:
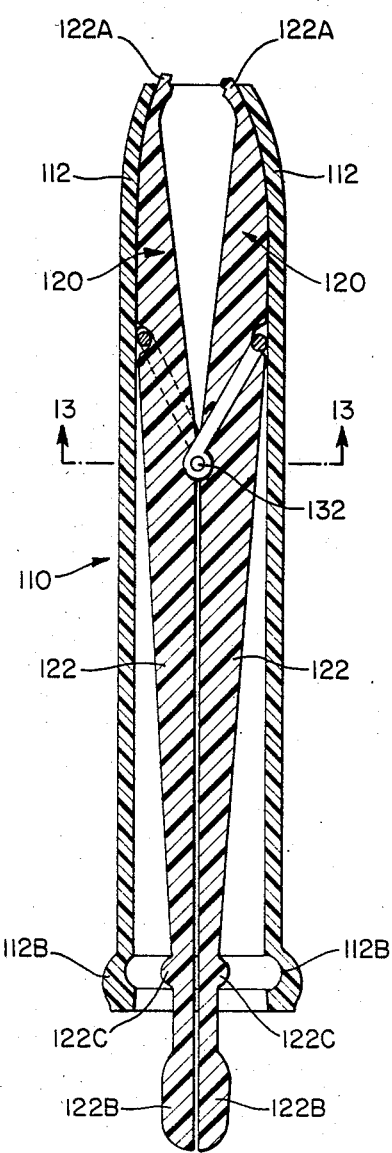
FIG. 11 is a side elevational view in section of the retraction device of FIG. 10 with the retraction elements shown in an open position.
Figure 12:
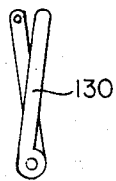
FIG. 12 is a side elevational view of the spring mechanism used in the retraction device of FIG. 10.
Figure 13:
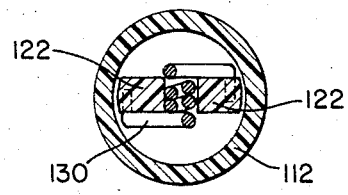
FIG. 13 is a sectional view taken along lines 11—11 of FIG. 11.

FIGS. 10-13 illustrate a second embodiment of the retraction device of the present invention. As shown in FIGS. 10 and 11, the retraction device of the second embodiment, referred to generally by reference numeral 110, includes an elongated tubular outer tube or barrel 112 and an internally contained retraction device element 120 which has a pair of arm portions 122. Arm portions 122 are spring loaded in a normally closed position within the barrel 112 by the action of spring element 130 secured to the arm portions by fastener 132. Spring element 130 is preferably a stainless steel spring. Elongated tubular barrel 112 includes a longitudinally extending center aperture 113 passing through the center thereof which opens at opposed upper and lower ends 113A and 113B, respectively. The barrel 112A is conically shaped at the open upper end 113A to facilitate insertion of the barrel 112 into the vagina. Similarly, the diameter of the open upper end 113A of the barrel is reduced from the diameter of the center aperture 113 which passes therethrough. The outer wall 112B of the barrel 112 is flared at its lower end 112C to facilitate gripping by the user.

The retraction device element 120 includes a pair of spring-loaded arm portions 122, each of which include a gripping edge 122A at one end thereof and gripping handles 122B at the opposite end thereof. A raised locking element or protrusion 122C is further provided on each arm portion proximately spaced from the gripping handle 122B and adapted to be received within an annular recess 112D formed around the interior wall of the barrel 112 complimentary to the flared lower end 112C. Capture of the locking elements 122C within the annular recess 112D of the barrel 112 prevents slippage of the retraction element 120 from the barrel 112 when it is in its normally closed position.

The retraction device 110 is adapted to operate in the following manner. The retraction device 110 is inserted into the woman's vagina with the gripping edges 122A of the retraction device element 120 in their spring-loaded normally closed position. Upon contact with the sponge to be retracted, the user then forces the gripping handles 122B together causing the gripping edges 122A to open and permit the gripping edges 122A to surround the sponge. Upon release of the gripping handles 122B, the spring 130 causes the gripping edges 122A to come together again in a closed position in order to grip the sponge and permit removal thereof.

Figure 14:
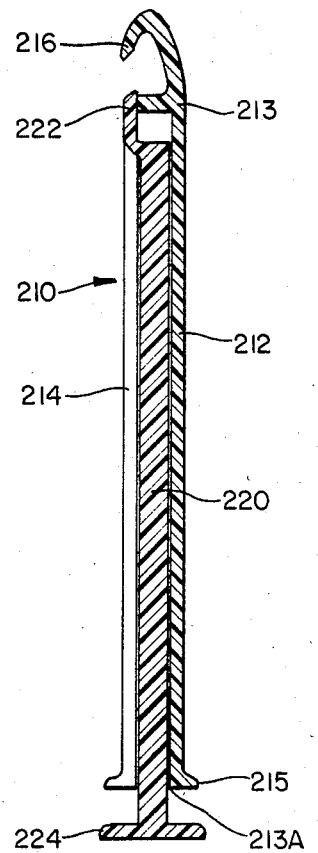
FIG. 14 is a side elevational view in section of another alternative embodiment of the retraction device of the present invention with the retraction element shown in an open position.
Figure 15:
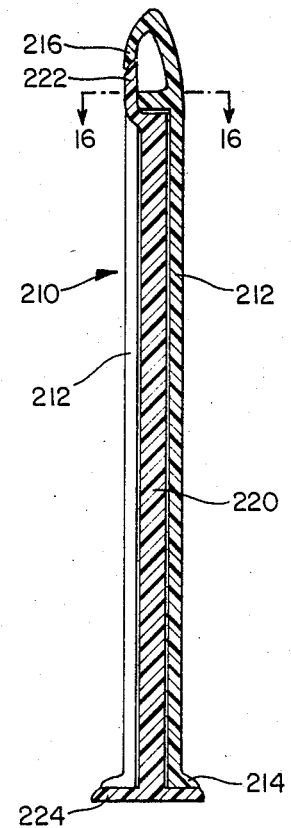
FIG. 15 is a sectional elevational view of the retraction device of FIG. 14 illustrated in a closed position.
Figure 16:
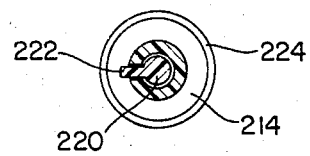
FIG. 16 is a sectional view taken along line 15—15 of FIG. 15.

Still another embodiment of the retraction device of the present invention, referred to generally by reference numeral 210, is illustrated in FIGS. 14-16. As shown, in particular in FIGS. 14 and 15, the retraction device 210 includes an elongated tubular outer tube or barrel 212 which contains a movable piston 220 therein. Elongated tubular barrel 212 includes a longitudinally extending center aperture 213 passing through the center thereof and is open at its upper and lower ends, 213B and 213A, respectively. An elongated, longitudinally extending keyway 214 is provided in the barrel 212 extending along the entire longitudinal extent thereof. An aerodynamically shaped, hook tip 216 is provided at the upper end of the barrel 212 and a gripping flange 215 is provided at the lower end thereof. The end of the hook tip 216 is curved downwardly toward the barrel 212.

A movable piston 220 is provided within the center aperture 213 of the barrel 212 adapted to be introduced through the open end 213A thereof. The movable piston 220 includes a tongue 222 which extends outwardly and at an angle relative to the piston 220. The tongue 222 is adapted to travel along the keyway 214 as the piston 220 is moved toward and away from the upper portion of the barrel 212. A T-shaped gripping handle 224 is provided at the end of the piston 220 opposite the tongue 222 and external to the barrel 212.

The retraction device 210 of the embodiment of FIGS. 14-16 is intended to operate in the following manner. As shown in FIG. 14, when the piston 20 is withdrawn out of the center aperture 213 of the barrel 212, the tongue 222 is drawn away from the hook tip 216 of the barrel which leaves a space therebetween for gripping the sponge or another object. As shown in FIG. 15, the aperture is closed by forcing the piston 220 back into the center aperture 213 of the barrel 212 which causes the tongue 222 to engage the hook tip 216 of the barrel 212 in order to grip and retain the sponge therebetween. The retraction device 210 can then be withdrawn from the vagina with the sponge attached thereto.

Having thus described the invention with particular reference to the preferred forms thereof, it will be obvious that various changes and modifications may be made therein without departing from the spirit and scope of the invention as defined by the appended claims.

Wherefore, I claim:

1. A reusable retraction device adapted to remove an object such as, for example, a vaginal sponge from a woman's vagina, said retraction device comprising:

an outer barrel open at its upper and lower ends with a longitudinally extending center aperture extending between said ends and a pin aperture extending transversely through the barrel and adapted to receive a retaining pin;

a tubular piston contained within said outer barrel and adapted to travel toward and away from the upper end of said barrel, said tubular piston being open at its upper end and having a T-shaped gripping handle at its opposed lower end which extends outwardly from the lower end of said barrel and in substantially the same plane as said barrel, said piston further including a pair of longitudinally extending, opposed keyway slots each proximately spaced from the upper end of the piston and adapted to permit said retaining pin to pass therethrough so as to capture the piston within said barrel; and a spring-loaded retraction element provided within the open upper end of said piston, said retraction element having a pair of gripping edges and including means for securing said retraction element to said retaining pin, said gripping edges being adapted to close when said piston is moved toward the upper end of the barrel and open when the piston is retracted from said upper end.

2. The retraction device of claim 1 wherein said barrel is open at both its upper and lower ends.

3. The retraction device of claim 2 wherein a gripping flange is provided about the lower open end of the barrel.

4. The retraction device of claim 2 wherein the upper end of said barrel is conically shaped to facilitate insertion into the vagina of a woman.

5. The retraction device of claim 1 wherein said retaining pin is adapted to extend through said outer barrel, said piston and said retraction device element.

6. The retraction device of claim 1 wherein said tubular piston includes a center aperture which extends between open upper and lower ends and wherein the center aperture at said upper end is flared.

7. The retraction device of claim 1 wherein said retraction element includes a pair of opposed arm portions each having at their respective ends at least one gripping edge.

8. The retraction device of claim 1 wherein said means for securing comprises retaining means provided between said arm portions.

9. The retraction device of claim 8 wherein a pin aperture is provided in said retaining means.

10. The retraction device of claim 1 wherein said retraction elements comprise stainless steel springs.

11. The retraction device of claim 10 wherein said springs are plastic-coated.

12. A reusable retraction device adapted to remove an object such as, for example, a vaginal sponge from a woman's vagina, said retraction device comprising:
   an outer barrel open at its upper and lower ends with a longitudinally extending center aperture extending between said open ends; and
   a retraction element contained within said barrel, said retraction element including a pair of spring loaded, retraction arms having normally closed gripping edges at their upper ends which extend out of the upper end of said barrel and normally separated gripping handles at their lower ends which extend out of the lower end of said barrel, said gripping edges adapted to open for gripping an object when the gripping handles are caused to be brought together and close and grip said object when the gripping handles are released and return to their normal separated position;
   said retraction element further including raised locking elements on said retraction element adapted to engage a complementary annular recess on an interior wall of said barrel to prevent slippage of the retraction device from the barrel.

13. A reusable retraction device adapted to remove an object such as, for example, a vaginal sponge from a woman's vagina, said retraction device comprising:
   an outer barrel open at its opposite ends and having a longitudinally extending center aperture extending therebetween, a longitudinally extending keyway opening into said center aperture and a hook tip at its upper end; and
   a movable piston contained within said outer barrel and adapted to travel toward and away from the upper end of said barrel, said piston including an outwardly projecting tongue adapted to travel in said keyway as said piston is moved toward and away from said upper end and further adapted to engage said hook tip for gripping said sponge when said piston is fully inserted into said barrel and be drawn away from said hook tip and release said sponge when said piston is retracted from said barrel, wherein said piston includes a T-shaped gripping handle at its lower end which extends outwardly from the lower end of said barrel and is in substantially the same plane as said barrel.

14. The retraction device of claim 13 wherein the end of said hook tip is curved downwardly toward said barrel.

15. The retraction device of claim 13 wherein a T-shaped gripping handle is provided at the lower end of the piston.

16. The retraction device of claim 13 wherein a gripping flange is provided at the lower end of the barrel.

* * * * *